United States Patent
Cardarelli et al.

(10) Patent No.: US 11,104,739 B2
(45) Date of Patent: Aug. 31, 2021

(54) COMBINATION THERAPY USING AN ANTI-FUCOSYL-GM1 ANTIBODY AND AN ANTI-CD137 ANTIBODY

(71) Applicant: BRISTOL-MYERS SQUIBB COMPANY, Princeton, NJ (US)

(72) Inventors: Josephine M. Cardarelli, San Carlos, CA (US); Daniel E. Lopes de Menezes, Berkeley, CA (US); Paul D. Ponath, San Francisco, CA (US); Bingliang Chen, Alameda, CA (US); Chin Pan, Los Altos, CA (US)

(73) Assignee: Bristol-Myers Squibb Company, Princeton, NJ (US)

(*) Notice: Subject to any disclaimer, the term of this patent is extended or adjusted under 35 U.S.C. 154(b) by 207 days.

(21) Appl. No.: 16/093,288

(22) PCT Filed: Apr. 14, 2017

(86) PCT No.: PCT/US2017/027663
§ 371 (c)(1),
(2) Date: Oct. 12, 2018

(87) PCT Pub. No.: WO2017/181034
PCT Pub. Date: Oct. 19, 2017

(65) Prior Publication Data
US 2019/0119395 A1 Apr. 25, 2019

Related U.S. Application Data

(60) Provisional application No. 62/322,407, filed on Apr. 14, 2016.

(51) Int. Cl.
| | | |
|---|---|---|
| *C07K 16/28* | (2006.01) | |
| *A61K 39/395* | (2006.01) | |
| *C07K 16/30* | (2006.01) | |
| *A61K 47/68* | (2017.01) | |
| *A61P 35/00* | (2006.01) | |

(52) U.S. Cl.
CPC .... *C07K 16/2878* (2013.01); *A61K 39/39533* (2013.01); *A61K 47/68* (2017.08); *A61P 35/00* (2018.01); *C07K 16/30* (2013.01); *C07K 2317/21* (2013.01); *C07K 2317/41* (2013.01); *C07K 2317/56* (2013.01); *C07K 2317/565* (2013.01); *C07K 2317/732* (2013.01); *C07K 2317/734* (2013.01); *C07K 2317/77* (2013.01)

(58) Field of Classification Search
CPC .............................. C07K 16/2878; A61P 35/00
See application file for complete search history.

(56) References Cited

U.S. PATENT DOCUMENTS

| | | | |
|---|---|---|---|
| 7,288,638 B2 | 10/2007 | Jure-Kunkel et al. | |
| 8,383,118 B2 * | 2/2013 | Vistica | A61K 45/06 424/141.1 |
| 8,475,790 B2 * | 7/2013 | Jure-Kunkel | C07K 16/2818 424/130.1 |
| 9,138,475 B2 * | 9/2015 | Vistica | C07K 16/3084 |
| 9,631,025 B2 * | 4/2017 | Vistica | A61P 35/00 |

FOREIGN PATENT DOCUMENTS

| | | | |
|---|---|---|---|
| WO | WO 2007067992 | * | 6/2007 |
| WO | WO 2014/028502 | * | 2/2014 |
| WO | WO2016049256 A1 | | 3/2016 |

OTHER PUBLICATIONS

Kohrt, et al., CD137 stimulation enhances the antilymphoma activity of anti-CD20 Antibodies, 2011, 117:2423-2432, Blood.
Lin et al., Fc-dependent expression of CD137 on human NK cells: insights into "agonistic" effects of anti-CD137 monoclonal antibodies, 2008, 112:699-707, Immunobiology.
Makkouk et al., Rationale for anti-CD137 cancer immunotherapy, 2016, 54:112-119, European Journal of Cancer.
Melero et al, Immunostimulatory monoclonal antibodies for cancer therapy, 2007, 7:95-106, Nature Reviews Cancer.
Molckovsky et al., First-in-class, first-in-human phase I results of targeted agents: Highlights of the 2008 American Society of Clinical Oncology Meeting, 2008, 20: 1-9, Journal of Hematology & Oncology.
Murillo et al., Therapeutic Antitumor Efficacy of Anti-CD137 Agonistic Monoclonal Antibody in Mouse Models of Myeloma, 2008, 14: 21: 6895-6906, Clinical Cancer Res.
Takeda et al., Combination Therapy of Established Tumors by Antibodies Targeting Immune Activating and Suppressing Molecules, 2010, 184: 1-9, The Journal of Immunology.

\* cited by examiner

*Primary Examiner* — Laura B Goddard
(74) *Attorney, Agent, or Firm* — Gregory R. Bellomy

(57) ABSTRACT

This disclosure provides combination therapy for treating a subject, such as a subject afflicted with a lung cancer, comprising administering to the subject an anti-fucosyl-GM1 antibody and an anti-CD137 antibody, or antigen-binding portions of either or both.

17 Claims, 3 Drawing Sheets
Specification includes a Sequence Listing.

SEQUENCE LISTING

<160> NUMBER OF SEQ ID NOS: 21

<210> SEQ ID NO 1

```
<211> LENGTH: 122
<212> TYPE: PRT
<213> ORGANISM: Homo sapiens

<400> SEQUENCE: 1

Glu Val Gln Leu Val Glu Ser Gly Gly Gly Ser Val Gln Pro Gly Glu
1               5                   10                  15

Ser Leu Arg Leu Ser Cys Val Ala Ser Gly Phe Thr Phe Ser Arg Tyr
            20                  25                  30

Lys Met Asn Trp Val Arg Gln Ala Pro Gly Lys Gly Leu Glu Trp Val
        35                  40                  45

Ser Tyr Ile Ser Arg Ser Gly Arg Asp Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Gly Thr Val Thr Thr Tyr Tyr Tyr Asp Phe Gly Met Asp Val Trp
            100                 105                 110

Gly Gln Gly Thr Thr Val Thr Val Ser Ser
        115                 120

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 3
<211> LENGTH: 451
<212> TYPE: PRT
<213> ORGANISM: Homo sapiens

<400> SEQUENCE: 3

Glu Val Gln Leu Val Glu Ser Gly Gly Gly Ser Val Gln Pro Gly Glu
1               5                   10                  15

Ser Leu Arg Leu Ser Cys Val Ala Ser Gly Phe Thr Phe Ser Arg Tyr
            20                  25                  30

Lys Met Asn Trp Val Arg Gln Ala Pro Gly Lys Gly Leu Glu Trp Val
        35                  40                  45

Ser Tyr Ile Ser Arg Ser Gly Arg Asp Ile Tyr Tyr Ala Asp Ser Val
50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Gly Thr Val Thr Thr Tyr Tyr Asp Phe Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 4
<211> LENGTH: 214
<212> TYPE: PRT
```

<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 5
<212> TYPE: PRT
<213> ORGANISM: Homo sapiens

<400> SEQUENCE: 5

Arg Tyr Lys Met Asn
1               5

<210> SEQ ID NO 6
<211> LENGTH: 17
<212> TYPE: PRT
<213> ORGANISM: Homo sapiens

<400> SEQUENCE: 6

Tyr Ile Ser Arg Ser Gly Arg Asp Ile Tyr Tyr Ala Asp Ser Val Lys
1               5                   10                  15

Gly

<210> SEQ ID NO 7
<211> LENGTH: 13
<212> TYPE: PRT
<213> ORGANISM: Homo sapiens

<400> SEQUENCE: 7

Thr Val Thr Thr Tyr Tyr Tyr Asp Phe Gly Met Asp Val

```
1               5                    10
```

<210> SEQ ID NO 8
<211> LENGTH: 11
<212> TYPE: PRT
<213> ORGANISM: Homo sapiens

<400> SEQUENCE: 8

```
Arg Ala Ser Gln Gly Ile Ser Ser Trp Leu Ala
1               5                   10
```

<210> SEQ ID NO 9
<211> LENGTH: 7
<212> TYPE: PRT
<213> ORGANISM: Homo sapiens

<400> SEQUENCE: 9

```
Ala Ala Ser Ser Leu Gln Ser
1               5
```

<210> SEQ ID NO 10
<211> LENGTH: 9
<212> TYPE: PRT
<213> ORGANISM: Homo sapiens

<400> SEQUENCE: 10

```
Gln Gln Tyr Asn Ser Tyr Pro Pro Thr
1               5
```

<210> SEQ ID NO 11
<211> LENGTH: 121
<212> TYPE: PRT
<213> ORGANISM: Homo sapiens

<400> SEQUENCE: 11

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120
```

<210> SEQ ID NO 12
<211> LENGTH: 109
<212> TYPE: PRT
<213> ORGANISM: Homo sapiens

<400> SEQUENCE: 12

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
                     20                  25                  30
Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Leu Thr Phe Gly Gly Gly Thr Lys Val Glu Ile Lys
            100                 105
```

<210> SEQ ID NO 13
<211> LENGTH: 447
<212> TYPE: PRT
<213> ORGANISM: Homo sapiens

<400> SEQUENCE: 13

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Ser Pro Glu Lys Gly Leu Glu Trp Ile
             35                  40                  45

Gly Glu Ile Asn His Gly Gly Tyr Val Thr Tyr Asn Pro Ser Leu Glu
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285
```

```
Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly
                435                 440                 445

<210> SEQ ID NO 14
<211> LENGTH: 216
<212> TYPE: PRT
<213> ORGANISM: Homo sapiens

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 15
<211> LENGTH: 5
<212> TYPE: PRT
<213> ORGANISM: Homo sapiens

<400> SEQUENCE: 15

Gly Tyr Tyr Trp Ser
1               5

<210> SEQ ID NO 16
<211> LENGTH: 16
<212> TYPE: PRT
<213> ORGANISM: Homo sapiens

<400> SEQUENCE: 16

Glu Ile Asn His Gly Gly Tyr Val Thr Tyr Asn Pro Ser Leu Glu Ser
1               5                   10                  15

<210> SEQ ID NO 17
<211> LENGTH: 13
<212> TYPE: PRT
<213> ORGANISM: Homo sapiens

<400> SEQUENCE: 17

Asp Tyr Gly Pro Gly Asn Tyr Asp Trp Tyr Phe Asp Leu
1               5                   10

<210> SEQ ID NO 18
<211> LENGTH: 11
<212> TYPE: PRT
<213> ORGANISM: Homo sapiens

<400> SEQUENCE: 18

Arg Ala Ser Gln Ser Val Ser Ser Tyr Leu Ala
1               5                   10

<210> SEQ ID NO 19
<211> LENGTH: 7
<212> TYPE: PRT
<213> ORGANISM: Homo sapiens

<400> SEQUENCE: 19

Asp Ala Ser Asn Arg Ala Thr
1               5

<210> SEQ ID NO 20
<211> LENGTH: 11
<212> TYPE: PRT
<213> ORGANISM: Homo sapiens

<400> SEQUENCE: 20

Gln Gln Arg Ser Asn Trp Pro Pro Ala Leu Thr
1               5                   10

<210> SEQ ID NO 21
<211> LENGTH: 255
<212> TYPE: PRT
<213> ORGANISM: Homo sapiens
<220> FEATURE:
<221> NAME/KEY: SIGNAL
<222> LOCATION: (1)..(17)
<220> FEATURE:
<221> NAME/KEY: mat_peptide
<222> LOCATION: (18)..(255)

```
<400> SEQUENCE: 21

Met Gly Asn Ser Cys Tyr Asn Ile Val Ala Thr Leu Leu Val Leu
        -15                 -10                  -5

Asn Phe Glu Arg Thr Arg Ser Leu Gln Asp Pro Cys Ser Asn Cys Pro
 -1   1              5                  10                  15

Ala Gly Thr Phe Cys Asp Asn Asn Arg Asn Gln Ile Cys Ser Pro Cys
                 20                  25              30

Pro Pro Asn Ser Phe Ser Ser Ala Gly Gly Gln Arg Thr Cys Asp Ile
             35              40                      45

Cys Arg Gln Cys Lys Gly Val Phe Arg Thr Arg Lys Glu Cys Ser Ser
         50                  55              60

Thr Ser Asn Ala Glu Cys Asp Cys Thr Pro Gly Phe His Cys Leu Gly
 65                  70                  75

Ala Gly Cys Ser Met Cys Glu Gln Asp Cys Lys Gln Gly Gln Glu Leu
 80              85                  90                  95

Thr Lys Lys Gly Cys Lys Asp Cys Cys Phe Gly Thr Phe Asn Asp Gln
                100                 105                 110

Lys Arg Gly Ile Cys Arg Pro Trp Thr Asn Cys Ser Leu Asp Gly Lys
             115             120             125

Ser Val Leu Val Asn Gly Thr Lys Glu Arg Asp Val Val Cys Gly Pro
        130             135                 140

Ser Pro Ala Asp Leu Ser Pro Gly Ala Ser Ser Val Thr Pro Pro Ala
    145             150                 155

Pro Ala Arg Glu Pro Gly His Ser Pro Gln Ile Ile Ser Phe Phe Leu
160             165                 170                 175

Ala Leu Thr Ser Thr Ala Leu Leu Phe Leu Leu Phe Phe Leu Thr Leu
            180             185                 190

Arg Phe Ser Val Val Lys Arg Gly Arg Lys Lys Leu Leu Tyr Ile Phe
            195             200             205

Lys Gln Pro Phe Met Arg Pro Val Gln Thr Thr Gln Glu Glu Asp Gly
        210             215                 220

Cys Ser Cys Arg Phe Pro Glu Glu Glu Glu Gly Gly Cys Glu Leu
    225             230                 235
```

COMBINATION THERAPY USING AN ANTI-FUCOSYL-GM1 ANTIBODY AND AN ANTI-CD137 ANTIBODY

FIELD OF THE INVENTION

The present invention relates to improved methods of treating cancer using a combination of therapeutic monoclonal antibodies.

BACKGROUND OF THE INVENTION

Fucosyl-GM1 is a sphingolipid monosialoganglioside composed of a ceramide lipid component, which anchors the molecule in the cell membrane, and a carbohydrate component that is exposed at the cell surface. Carbohydrate antigens are the most abundantly expressed antigens on the cell surface of cancers (Feizi T. (1985) *Nature* 314:53-7). In some tumor types, such as small cell lung cancer (SCLC), initial responses to chemotherapy are impressive, but chemo-refractory relapses rapidly follows. Intervention with novel immunotherapeutics may succeed in overcoming drug resistant relapse (Johnson D H. (1995) *Lung Cancer* 12 Suppl 3:S71-5). Several carbohydrate antigens, such as gangliosides GD3 and GD2, have been shown to function as effective targets for passive immunotherapy with mAbs (Irie R F and Morton D L. (1986) *PNAS* 83:8694-8698; Houghton A N et al. (1985) *PNAS* 82:1242-1246). Ganglioside antigens have also been demonstrated to be effective targets for active immunotherapy with vaccines in clinical trials (Krug L M et al. (2004) *Clinical Cancer Research* 10:6094-6100; Dickler M N et al. (1999) *Clinical Cancer Research* 5:2773-2779; Livingston P O et al. (1994) *J. Clin. Oncol.* 12:1036-44). Indeed, serum derived from SCLC patients who developed antibody titers to fucosyl-GM1 following vaccination with KLH conjugated antigen, demonstrated specific binding to tumor cells and tumor specific complement dependent cytotoxicity (CDC). Anti-fucosyl-GM1 titer associated toxicities were mild and transient and three patients with limited-stage SCLC were relapse-free at 18, 24, and 30 months (Krug et al., supra; Dickler et al., supra).

Fucosyl-GM1 expression has been shown in a high percentage of SCLC cases and unlike other ganglioside antigens, fucosyl-GM1 has little or no expression in normal tissues (Nilsson et al. (1984) *Glycoconjugate J.* 1:43-9; Krug et al., supra; Brezicka et al. (1989) *Cancer Res.* 49:1300-5; Zhangyi et al. (1997) *Int. J. Cancer* 73:42-49; Brezicka et al. (2000) *Lung Cancer* 28:29-36; Fredman et al. (1986) *Biochim. Biophys. Acta* 875: 316-23; Brezicka et al. (1991) *APMIS* 99:797-802; Nilsson et al. (1986) *Cancer Res.* 46:1403-7). The presence of fucosyl-GM1 has been demonstrated in culture media from SCLC cell lines, in tumor extracts and serum of nude mouse xenografts and in the serum of SCLC patients with extensive-stage disease (Vangsted et al. (1991) *Cancer Res.* 51:2879-84; Vangsted et al. (1994) *Cancer Detect. Prev.* 18:221-9). Fucosyl-GM1 expression has also been observed in a significant fraction of non-small cell lung cancer (NSCLC) samples. WO 07/067992. These reports provide convincing evidence for fucosyl-GM1 as a highly specific tumor antigen, which may be targeted by an immunotherapeutic.

An antibody that recognizes fucosyl-GM1 on cancer cells and directs their destruction, anti-fucosyl GM1 mAb BMS-986012, has entered clinical trials for the treatment of subjects with relapsed/refractory small cell lung cancer (NCT02247349). See Molckovsky & Siu (2008) *J. Hematol. Oncol.* 1:20. BMS-986012 is a non-fucosylated antibody and thus exhibits enhanced ADCC compared to an antibody with typical mammalian glycosylation. Although effective as a single agent, there exists a need for even more effective cancer therapy based on targeting of fucosyl GM1-expressing cancer cells.

SUMMARY OF THE INVENTION

The present invention provides methods for treating a subject afflicted with cancer, such as a lung cancer, including small cell lung cancer (SCLC), comprising administering to the subject a therapeutically effective combination of agents, such as monoclonal antibodies or an antigen-binding portions thereof, that specifically bind to fucosyl-GM1 and CD137. In one embodiment the anti-fucosyl-GM1 antibody is hypofucosylated or non-fucosylated.

In some embodiments, the anti-fucosyl-GM1 mAb competes with BMS-986012, comprises the same CDRs as BMS-986012, comprises the same heavy and light chain variable domains as BMS-986012, comprises the same heavy and light chains as BMS-986012, is BMS-986012, or is an antibody drug conjugate of BMS-986012. In one embodiment, the anti-CD137 mAb competes with BMS-663513, comprises the same CDRs as BMS-663513, comprises the same heavy and light chain variable domains as BMS-663513, or is BMS-663513.

In one aspect, the invention provides methods of combination therapy with anti-fucosyl GM1 and anti-CD137 agents comprising administration of the anti-fucosyl GM1 agent, such as BMS-986012, concurrently with administration of the anti-CD137 agent.

In a distinct aspect, the invention provides methods of combination therapy with anti-fucosyl GM1 and anti-CD137 agents comprising administration of the anti-fucosyl GM1 agent, such as BMS-986012, prior to, rather than concurrently with, the anti-CD137 agent, such as BMS-663513. In various embodiments, the anti-fucosyl GM1 agent is first administered 0.5, 1, 2, 4, and 7 days prior to first administration of the anti-CD137 agent. In various other embodiments, the anti-fucosyl GM1 agent is administered at days 1, 22, 43, 64 and 85 and the anti-CD137 agent is administered at days 2, 23, 44, 65 and 86.

In some embodiments, the combination therapy of the present invention is administered to a subject (e.g. a human subject) who suffers from small cell lung cancer (SCLC). In one embodiment, the subject has previously received an initial anti-cancer therapy. In another embodiment, the lung cancer is an advanced, metastatic, relapsed, and/or refractory lung cancer.

In certain embodiments, the anti-fucosyl-GM1 mAb is administered at a dose ranging from 10 to 2000 mg once every 1, 2, 3 or 4 weeks. In one embodiment, the anti-fucosyl-GM1 mAb is administered at a dose ranging from 400 to 1000 mg once every 3 weeks, with administration of anti-CD137 mAb at a dose ranging from 1 to 10 mg, e.g. 3 to 8 mg, one day after each dose of anti-fucosyl-GM1 mAb. In various embodiments, the dose of the anti-fucosyl GM1 mAb is 2-, 10-, 30- or 1000-fold higher than the dose of anti-CD137 mAb on a weight basis.

In various embodiments, the method comprises one, two, three or four treatments, or is continued for as long as clinical benefit is observed or until unmanageable toxicity or disease progression occurs.

In one embodiment, one or both of the antibodies are formulated for intravenous administration. The efficacy of the treatment methods provided herein can be assessed using any suitable means, such as reduction in size of the cancer, reduction in number of metastatic lesions over time, complete response, partial response, and stable disease.

Other features and advantages of the instant invention will be apparent from the following detailed description and examples, which should not be construed as limiting. The contents of all cited references, including scientific articles, newspaper reports, GenBank entries, patents and patent applications cited throughout this application are expressly incorporated herein by reference in their entireties.

DETAILED DESCRIPTION OF THE INVENTION

Figure 1:
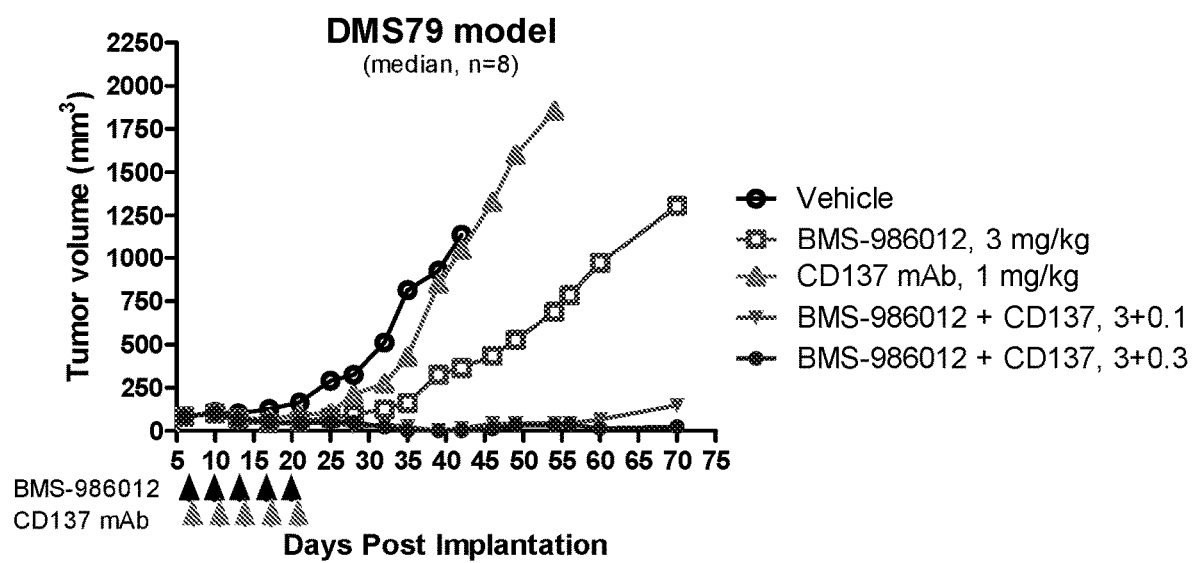
FIG. 1 shows tumor growth in the mouse DMS79 tumor model as a function of treatment with anti-fucosyl GM1 BMS-986012 and/or anti-muCD137 antibodies. Median tumor volumes are presented for groups of 8 mice at each data point. See Example 1.

BMS-986012 is a first-in-class fully human monoclonal antibody (mAb) that specifically binds to the fucosyl-GM1 (fuc-GM1) ganglioside. BMS-986012 exhibits high-affinity and dose-dependent saturable binding to fuc-GM1 and shows no detectable antigen-specific binding to closely related molecule GM1. Because fucosyl GM1 is preferentially found on the surface of lung cancer cells, BMS-986012 is particularly well suited to treating lung cancer, such as small cell lung cancer (SCLC). BMS-986012, as used herein, always refers to a non-fucosylated antibody whether or not that is expressly stated.

BMS-986012 is non-fucosylated (lacking fucosylation on the Fc domain). The absence of the fucosyl group in BMS-986012 confers higher affinity for Fc receptors resulting in enhanced antibody-dependent cellular cytotoxicity (ADCC). Furthermore, the antibody was shown to mediate potent complement dependent cytotoxicity (CDC) as well as antibody-dependent cellular phagocytosis (ADCP). See, e.g., WO 2007/067992, the content of which is expressly incorporated herein by reference in its entirety.

Although BMS-986012 is effective as monotherapy in treatment of lung cancer, improved methods of treatment are always desired.

CD137 (4-1BB) is a T cell co-stimulatory receptor induced on TCR activation. Nam et al. (2005) *Curr. Cancer Drug Targets* 5:357; Watts et al. (2005) *Ann. Rev. Immunol.* 23:23. In addition to its expression on activated CD4$^+$ and CD8$^+$ T cells, CD137 is also expressed on CD4$^+$CD25$^+$ regulatory T cells, activated natural killer (NK) and NK-T cells, monocytes, neutrophils, and dendritic cells. Its natural ligand, CD137L, has been described on antigen-presenting cells including B cells, monocyte/macrophages, and dendritic cells. Watts et al. (2005) *Ann. Rev. Immunol.* 23:2. On interaction with its ligand, CD137 leads to increased TCR-induced T-cell proliferation, cytokine production, functional maturation, and prolonged CD8$^+$ T-cell survival. Nam et al. (2005) *Curr. Cancer Drug Targets* 5:357; Watts et al. (2005) *Ann. Rev. Immunol.* 23:23. Use of antibodies to activate the CD137 pathway for treating cancer has entered clinical trials. Li et al. (2013) *Clin. Pharmacol.* 5(Suppl 1):47; Sznol et al. (2008) *J. Clin. Oncol.* 26(Suppl. 15):3007.

Applicants observed that administration of anti-fucosyl GM1 antibody to a mixture of DMS-79 (fucosyl GM1-expressing) tumor cells and NK cells in vitro induced a dose-dependent enhancement in CD137 expression on the NK cells, increasing the percentage of CD137$^+$ NK cells from less than 4% to over 35% at the highest doses (data not shown). See also Kohrt et al. (2011) *Blood* 117:2423 (disclosing a similar effect with anti-CD20); Lin et al. (2008) *Blood* 112:699. Without intending to be limited by theory, it is possible that BMS-986012 bound to fucosyl GM1 on tumor cells also binds to Fc receptors on NK cells, and that this interaction with the NK cell Fc receptor is what triggers increased CD137 expression. Because CD137 is an activator of NK cells, CD137 agonism might be helpful in enhancing NK cell-mediated anti-tumor effects. See U.S. Pat. No. 7,288,638; Melero et al. (2007) *Nat. Rev. Cancer* 7:95; Takeda et al. (2010) *J. Immunol.* 184:5493; Murillo et al. (2008) *Clin. Cancer Res.* 14:6895. Combination therapy methods of present invention are based on increasing CD137 signaling, for example using an agonist anti-CD137 antibody, and the enhancement of this effect by prior or concurrent administration of anti-fucosyl GM1 antibodies to increase CD137 expression on NK cells, thus maximizing the effect of anti-CD137 therapy. Equivalently, the invention may be viewed as augmenting the anti-tumor (cell killing) effect of anti-fucosyl GM1 antibody by administering an agonist anti-CD137 antibody that enhances the NK cell-mediated anti-tumor effects.

The specific combination of anti-fucosyl GM1 antibody with anti-CD137 antibody is particularly beneficial because treatment with anti-fucosyl GM1 antibody enhances CD137 expression on NK cells, maximizing the effect of the agonist anti-CD137 antibody. One benefit of such combination therapy is that it may preferentially direct the effects of agonist anti-CD137 therapy toward the desired target cells (fucosyl GM1-expressing lung cancer cells) by enhancing their CD137 expression, and away from general systemic NK cell stimulation that may give rise to immune-mediated side effects. Kohrt et al. (2011) *Blood* 117:2423. Such targeting may allow for lower dosing of agonist CD137 antibodies, thus minimizing undesired toxicities.

In some embodiments of the present invention, the anti-fucosyl GM1 antibody is administered prior to administration of anti-CD137 antibody. Without intending to be limited by theory, such pre-treatment with anti-fucosyl GM1 antibody allows binding to fucosyl GM1 on target tumor cells, ligation of the Fc region of the anti-fucosyl GM1 antibody to Fc receptors on NK cells, and most importantly upregulation of CD137 on NK cells, prior to administration of anti-CD137. As a consequence, at the (subsequent) time of dosing with anti-CD137 there exists in the subject a pre-existing population of NK cells in proximity to the target tumor cells and with elevated CD137 expression, such that binding (and effects) of anti-CD137 will be preferentially directed to the target tumor cells.

I. Definitions

In order that the present disclosure may be more readily understood, certain terms are first defined. As used in this application, except as otherwise expressly provided herein, each of the following terms shall have the meaning set forth below. Additional definitions are set forth throughout the application.

"BMS-986012," as used herein, refers to a non-fucosylated anti-fucosyl GM1 mAb comprising heavy chains of SEQ ID NO: 3 and light chains of SEQ ID NO: 4. BMS-986012 also comprises heavy chain variable domains of SEQ ID NO: 1 and light chain variable domains of SEQ ID NO: 2. BMS-986012 also comprises CDR sequences of SEQ ID NO: 5 (CDRH1), SEQ ID NO: 6 (CDRH2), SEQ ID NO: 7 (CDRH3), SEQ ID NO: 8 (CDRL1), SEQ ID NO: 9 (CDRL2), SEQ ID NO: 10 (CDRL3).

"BMS-6633513," as used herein, refers to an anti-CD137 mAb comprising heavy chains of SEQ ID NO: 13 and light chains of SEQ ID NO: 14, also known as urelumab. BMS-6633513 also comprises heavy chain variable domains of SEQ ID NO: 11 and light chain variable domains of SEQ ID NO: 12. BMS-6633513 also comprises CDR sequences of SEQ ID NO: 15 (CDRH1), SEQ ID NO: 16 (CDRH2), SEQ ID NO: 17 (CDRH3), SEQ ID NO: 18 (CDRL1), SEQ ID NO: 19 (CDRL2), SEQ ID NO: 20 (CDRL3).

Target proteins referenced herein (also referred to as antigens), such as CD137, are intended to refer to their human orthologs (e.g. huCD137; NP_001552; GeneID 3604) unless otherwise indicated or clear from the context.

"Administering" refers to the physical introduction of a composition comprising a therapeutic agent to a subject, using any of the various methods and delivery systems known to those skilled in the art. Preferred routes of administration for the anti-fucosyl-GM1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. The TKI is typically administered via a non-parenteral route, preferably orally. Other non-parenteral routes include a topical, epidermal or mucosal route of administration, for example, intranasally, vaginally, rectally, sublingually or topically. Administering can also be performed, for example, once, a plurality of times, and/or over one or more extended periods. Dose intervals denominated in "days" are intended to represent approximately 24 hour intervals, but may vary slightly due to scheduling difficulties or other delays in administration.

"Concurrent" administration refers to dosing of two distinct agents, such as anti-fucosyl GM1 and anti-CD137 antibodies, at or around the same time rather than intentionally delaying administration of one of the agents. As such, concurrent administration includes simultaneous administration, e.g. when the agents are co-formulated or mixed prior to administration, and also includes administration of the two drugs within a convenient interval, typically during the same visit to a health care facility. Typically concurrent administration is performed on the same day, and excludes administration at separate visits to a health care facility.

An "adverse event" (AE) as used herein is any unfavorable and generally unintended or undesirable sign (including an abnormal laboratory finding), symptom, or disease associated with the use of a medical treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin that binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. Sequences of antibody heavy chains herein may comprise a C-terminal lysine (K) residue but that residue may be clipped off during manufacture, entirely or partially, or it may be removed from the genetic construct used to produce the antibody so as to avoid potential heterogeneity arising from the aforementioned clipping. Both heavy chain sequences provided herein (SEQ ID NOs: 3 and 13) do not include C-terminal lysine residues.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "isolated antibody" refers to an Ab that is substantially free of other Abs having different antigenic specificities (e.g., an isolated Ab that binds specifically to fucosyl-GM1 is substantially free of Abs that bind specifically to antigens other than fucosyl-GM1). Moreover, an isolated Ab may be substantially free of other cellular material and/or chemicals.

The term "monoclonal antibody" ("mAb") refers to a non-naturally occurring preparation of Ab molecules of single molecular composition, i.e., Ab molecules whose primary sequences are essentially identical, and which exhibits a single binding specificity and affinity for a particular epitope. A mAb is an example of an isolated Ab.

MAbs may be produced by hybridoma, recombinant, transgenic or other techniques known to those skilled in the art.

A "human" antibody (HuMAb) refers to an Ab having variable regions in which both the framework and CDR regions are derived from human germline immunoglobulin sequences. Furthermore, if the Ab contains a constant region, the constant region also is derived from human germline immunoglobulin sequences. The human Abs of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include Abs in which CDR sequences derived from the germline of another mammalian species, such as a mouse, have been grafted onto human framework sequences. The terms "human" Abs and "fully human" Abs and are used synonymously.

A "humanized antibody" refers to an Ab in which some, most or all of the amino acids outside the CDR domains of a non-human Ab are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

A "chimeric antibody" refers to an Ab in which the variable regions are derived from one species and the constant regions are derived from another species, such as an Ab in which the variable regions are derived from a mouse Ab and the constant regions are derived from a human Ab.

An "anti-antigen" Ab refers to an Ab that binds specifically to the antigen. For example, an anti-fucosyl-GM1 Ab binds specifically to fucosyl-GM1.

An "antigen-binding portion" of an Ab (also called an "antigen-binding fragment") refers to one or more fragments of an Ab that retain the ability to bind specifically to the same antigen bound by the whole Ab.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream. The terms, "cancer," "tumor," and "neoplasm," are used interchangeably herein.

A "subject" includes any human or nonhuman animal. The term "nonhuman animal" includes, but is not limited to, vertebrates such as nonhuman primates, sheep, dogs, and rodents such as mice, rats and guinea pigs. In preferred embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example, an "anti-cancer agent" promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent preferably inhibits cell growth or tumor growth by at least about 20%, more preferably by at least about 40%, even more preferably by at least about 60%, and still more preferably by at least about 80% relative to untreated subjects. In other preferred embodiments of the invention, tumor regression may be observed and continue for a period of at least about 20 days, more preferably at least about 40 days, or even more preferably at least about 60 days. Notwithstanding these ultimate measurements of therapeutic effectiveness, evaluation of immunotherapeutic drugs must also make allowance for "immune-related" response patterns.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In preferred embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated. Such ranges further include the values as the boundaries of the ranges.

Various aspects of the invention are described in further detail in the following subsections.

II. Anti-Fucosyl-GM1 Antibodies

HuMAbs that bind specifically to fucosyl-GM1 with high affinity have been disclosed in U.S. Pat. No. 8,383,118 and WO 2007/067992 (e.g., human monoclonal antibodies 5B1, 5B1a, 7D4, 7E4, 13B8 and 18D5). Each of the HuMAbs disclosed in U.S. Pat. No. 8,383,118 has been demonstrated to exhibit one or more desirable functional properties: (1) specifically binds to fucosyl-GM1; (2) binds to fucosyl-GM1 with high affinity (for example with a $K_D$ of $1 \times 10^{-7}$ M or less); (c) binds to the human small cell lung cancer cell line DMS-79 (Human SCLC ATCC # CRL-2049); and (d) inhibit growth of tumor cells in vitro or in vivo. Preferably, the antibody binds to fucosyl-GM1 with a $K_D$ of $5 \times 10^{-8}$ M or less, binds to fucosyl-GM1 with a $K_D$ of $1 \times 10^{-8}$ M or less, binds to fucosyl-GM1 with a $K_D$ of $5 \times 10^{-9}$ M or less, or binds to fucosyl-GM1 with a $K_D$ of between $1 \times 10^{-8}$ M and $1 \times 10^{-10}$ M or less. Standard assays to evaluate the binding ability of the antibodies toward fucosyl-GM1 are known in the art, including for example, ELISAs, Western blots and RIAs. The binding kinetics (e.g., binding affinity) of the antibodies also can be assessed by standard assays known in the art, such as by ELISA, Scatchard and Biacore analysis.

A preferred anti-fucosyl-GM1 Ab is BMS-986012 (also referred to as MDX-1110 or 7E4).

Anti-fucosyl-GM1 Abs usable in the disclosed methods also include isolated Abs that bind specifically to fucosyl-GM1 and compete for binding to fucosyl-GM1 with BMS-986012 (see, e.g., U.S. Pat. No. 8,383,118; WO 2007/067992). The ability of Abs to compete for binding to an antigen indicates that these Abs bind to the same epitope region of the antigen and sterically hinder the binding of other competing Abs to that particular epitope region. These competing Abs are expected to have functional properties very similar those of BMS-986012 by virtue of their binding to the same epitope region of fucosyl-GM1. Competing Abs can be readily identified based on their ability to compete with BMS-986012 in standard fucosyl-GM1 binding assays such as Biacore analysis, ELISA assays or flow cytometry (see, e.g., WO 2013/173223).

For administration to human subjects, these Abs are preferably chimeric Abs, or more preferably humanized or human Abs. Such chimeric, humanized or human mAbs can be prepared and isolated by methods well known in the art. Anti-fucosyl-GM1 Abs usable in the methods of the disclosed invention also include antigen-binding portions of the above Abs. It has been amply demonstrated that the antigen-binding function of an Ab can be performed by fragments of a full-length Ab. Examples of binding fragments encompassed within the term "antigen-binding portion" of an Ab include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an Ab. Anti-fucosyl-GM1 antibodies (or VH and/or VL domains derived therefrom) suitable for use in the invention can be generated using methods well known in the art.

An exemplary anti-fucosyl-GM1 antibody is BMS-986012 comprising heavy and light chains comprising the sequences shown in SEQ ID NOs: 3 and 4, respectively, or antigen binding fragments and variants thereof.

In other embodiments, the antibody has heavy and light chain CDRs or variable regions of BMS-986012. Accordingly, in one embodiment, the antibody comprises CDR1, CDR2, and CDR3 domains of the VH of BMS-986012 having the sequence set forth in SEQ ID NO: 1, and CDR1, CDR2 and CDR3 domains of the VL of BMS-986012 having the sequence set forth in SEQ ID NO: 2. In another embodiment, the antibody comprises the heavy chain CDR1, CDR2 and CDR3 domains comprising the sequences set forth in SEQ ID NOs: 5, 6, and 7, respectively, and the light chain CDR1, CDR2 and CDR3 domains comprising the sequences set forth in SEQ ID NOs: 8, 9, and 10, respectively. In another embodiment, the antibody comprises VH and VL regions comprising the amino acid sequences set forth in SEQ ID NO: 1 and SEQ ID NO: 2, respectively. In another embodiment, the antibody competes for binding with and/or binds to the same epitope on fucosyl-GM1 as the above-mentioned antibodies. In another embodiment, the antibody has at least about 90% variable region amino acid sequence identity with the above-mentioned antibodies (e.g., at least about 90%, 95% or 99% variable region identity with SEQ ID NO: 1 or SEQ ID NO: 2).

III. Non-Fucosylation and Hypofucosylation

The interaction of antibodies with FcγRs can be enhanced by modifying the glycan moiety attached to each Fc fragment at the N297 residue. In particular, the absence of branching fucose residues strongly enhances ADCC via improved binding of IgG to activating FcγRIIIA without altering antigen binding or CDC. Natsume et al. (2009) *Drug Des. Devel. Ther.* 3:7. There is convincing evidence that afucosylated tumor-specific antibodies translate into enhanced therapeutic activity in mouse models in vivo. Nimmerjahn & Ravetch (2005) *Science* 310:1510; Mossner et al. (2010) *Blood* 115:4393.

Modification of antibody glycosylation can be accomplished by, for example, expressing the antibody in a host cell with altered glycosylation machinery. Antibodies with reduced or eliminated fucosylation, which exhibit enhanced ADCC, are particularly useful in the methods of the present invention. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (α-(1,6) fucosyltransferase (see U.S. Pat. App. Publication No. 20040110704; Yamane-Ohnuki et al. (2004) *Biotechnol. Bioeng.* 87: 614), such that antibodies expressed in these cell lines lack fucose on their carbohydrates. As another example, EP 1176195 also describes a cell line with a functionally disrupted FUT8 gene as well as cell lines that have little or no activity for adding fucose to the N-acetylglucosamine that binds to the Fc region of the antibody, for example, the rat myeloma cell line YB2/0 (ATCC CRL 1662). PCT Publication WO 03/035835 describes a variant CHO cell line, Lec13, with reduced ability to attach fucose to Asn(297)-linked carbohydrates, also resulting in hypofucosylation of antibodies expressed in that host cell. See also Shields et al. (2002) *J. Biol. Chem.* 277:26733. Antibodies with a modified glycosylation profile can also be produced in chicken eggs, as described in PCT Publication No. WO 2006/089231. Alternatively, antibodies with a modified glycosylation profile can be produced in plant cells, such as *Lemna*. See e.g. U.S. Publication No. 2012/0276086. PCT Publication No. WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies. See also Umaña et al. (1999) *Nat. Biotech.* 17:176. Alternatively, the fucose residues of the antibody may be cleaved off using a fucosidase enzyme. For example, the enzyme alpha-L-fucosidase removes fucosyl residues from antibodies. Tarentino et al. (1975) *Biochem.* 14:5516. Antibodies with reduced fucosylation may also be produced in cells harboring a recombinant gene encoding an enzyme that uses GDP-6-deoxy-D-lyxo-4-hexylose as a substrate, such as GDP-6-deoxy-D-lyxo-4-hexylose reductase (RMD), as described at U.S. Pat. No. 8,642,292. Alternatively, cells may be grown in medium containing fucose analogs that block the addition of fucose residues to the N-linked glycan or a glycoprotein, such as antibody, produced by cells grown in the medium. U.S. Pat. No. 8,163,551; WO 09/135181.

IV. Anti-CD137 Antibodies

HuMAbs that bind specifically to human CD137 with high affinity have been disclosed and claimed in U.S. Pat. No. 7,288,638 (human monoclonal antibodies human 4-1BB, also known as CD137). The sequences of anti-huCD137 mAb BMS-663513 are provided herein at SEQ ID NOs: 11-20.

Anti-huCD137 antibody BMS-663513 is a powerful CD137 agonist driving immune response and as a consequence must be administered at a relatively low dose to avoid immune-mediated side effects. In specific embodiments of monotherapy using BMS-663513, the antibody is administered at a flat doses between 1 mg and 10 mg, e.g. 3 mg or 8 mg, at intervals of every 4 or 8 weeks. See WO 2016/029073. In other embodiments BMS-663513 can be administered at between 0.05 and 1 mg/kg, e.g. 0.1 or 0.3 mg/kg.

Anti-huCD137 Abs usable in the disclosed methods also include isolated Abs that bind specifically to CD137 and compete for binding to CD137 with BMS-663513. The ability of Abs to compete for binding to an antigen indicates that these Abs bind to the same epitope region of the antigen and sterically hinder the binding of other competing Abs to that particular epitope region. These competing Abs are expected to have functional properties very similar those of BMS-663513 by virtue of their binding to the same epitope region of CD137. Competing Abs can be readily identified based on their ability to compete with BMS-663513 in standard binding assays such as Biacore analysis, ELISA assays or flow cytometry.

For administration to human subjects, these Abs are preferably chimeric Abs, or more preferably humanized or human Abs. Such chimeric, humanized or human mAbs can be prepared and isolated by methods well known in the art. Anti-huCD137 Abs usable in the methods of the disclosed invention also include antigen-binding portions of the above Abs. Examples of binding fragments encompassed within the term "antigen-binding portion" of an Ab include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an Ab.

V. Antibodies that Compete with Reference Antibodies

Antibodies that compete with anti-fucosyl GM1 mAb BMS-986012 or anti-CD137 mAb BMS-663513 and for binding to their respective antigens may be determined using methods well known in the art, for example in an enzyme linked immunosorbent assay (ELISA) or by fluorescence-activated cell sorting (FACS).

An exemplary competition experiment to determine whether a test antibody "competes with" a reference antibody (BMS-986012 or BMS-663513) may be conducted as follows: cells expressing the antigen (fucosyl-GM1 or CD137) are seeded at $10^5$ cells per sample well in a 96 well plate. The plate is set on ice followed by the addition of unconjugated test antibody at concentrations ranging from 0 to 50 μg/mL (three-fold titration starting from a highest concentration of 50 μg/mL). An unrelated IgG may be used as an isotype control for the first antibody and added at the same concentrations (three-fold titration starting from a highest concentration of 50 μg/mL). A sample pre-incubated with 50 μg/mL unlabeled reference antibody may be included as a positive control for complete blocking (100% inhibition) and a sample without antibody in the primary incubation may be used as a negative control (no competition; 0% inhibition). After 30 minutes of incubation, labeled, e.g., biotinylated, reference antibody is added at a concentration of 2 μg/mL per well without washing. Samples are incubated for another 30 minutes on ice. Unbound antibodies are removed by washing the cells with FACS buffer. Cell-bound labeled reference antibody is detected with an agent that detects the label, e.g., PE conjugated streptavidin (Invitrogen, catalog #521388) for detecting biotin. The samples are acquired on a FACS Calibur Flow Cytometer (BD, San Jose) and analyzed with Flowjo software (Tree Star, Inc., Ashland, Oreg.). The results may be represented as % inhibition.

Unless otherwise indicated, an antibody will be considered to compete with a reference antibody (BMS-986012 or BMS-663513) if it reduces binding of the selected antibody to its respective antigen by at least 20% when used at a roughly equal molar concentration with the reference antibody, as measured in a competition ELISA as outlined in the preceding paragraph.

VI. Pharmaceutical Compositions

Therapeutic agents (e.g., anti-fucosyl-GM1 antibodies and/or anti-CD137 antibodies, or antigen binding fragments thereof) of the present invention may be constituted in a composition, e.g., a pharmaceutical composition containing and a pharmaceutically acceptable carrier. Pharmaceutical compositions of the present invention include both individual antibodies and co-formulations.

As used herein, a "pharmaceutically acceptable carrier" includes any and all solvents, dispersion media, coatings, antibacterial and antifungal agents, isotonic and absorption delaying agents, and the like that are physiologically compatible. "Pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil, glycerol polyethylene glycol ricinoleate, and the like. Water or aqueous solution saline and aqueous dextrose and glycerol solutions may be employed as carriers, particularly for injectable solutions (e.g., comprising an anti-fucosyl-GM1 antibody). Preferably, the carrier for a composition containing an Ab is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and non-aqueous carriers, and/or adjuvants such as preservatives, wetting agents, emulsifying agents and dispersing agents.

Liquid compositions for parenteral administration can be formulated for administration by injection or continuous infusion. Routes of administration by injection or infusion include intravenous, intraperitoneal, intramuscular, intrathecal and subcutaneous. In one embodiment, the anti-fucosyl-GM1 antibody is administered intravenously.

VII. Methods of Treatment

Provided herein are clinical methods for treating a lung cancer (e.g., small cell lung cancer) in a subject (e.g., a human subject), comprising administering to the subject a therapeutically effective amounts of an anti-fucosyl-GM1 antibody, or an antigen-binding portion thereof and an anti-huCD137 antibody, or an antigen-binding portion thereof. In one embodiment, the subject has previously received an initial anti-cancer therapy. In another embodiment, the lung cancer is an advanced, metastatic, relapsed, and/or refractory lung cancer.

In a particular embodiment, the anti-fucosyl-GM1 antibody is BMS-986012. In some embodiments, the anti-huCD137 antibody is BMS-663513. In another embodiment, dosage regimens are adjusted to provide the optimum desired response (e.g., an effective response).

In another embodiment, the antibody is administered as a first line of treatment (e.g., the initial or first treatment). In another embodiment, the antibody is administered as a second line of treatment (e.g., after the initial or first treatment, including after relapse and/or where the first treatment has failed).

In certain embodiments, the anti-fucosyl-GM1 antibody is administered at a dose ranging from 10 to 2000 mg once every 1, 2, 3 or 4 weeks. For example, the antibody is administered at a dose ranging from 20 to 1000 mg once every 3 weeks. Optionally, the method comprises at least one treatment cycle of three weeks. For example, the method comprises at least four treatment cycles of three weeks. To illustrate, the antibody is administered on Days 1, 22, 43, and 64.

In certain specific embodiments, the antibody is administered according to at least one of the following dosing regimens: (a) about 20 mg of the antibody every 3 weeks; (b) about 70 mg of the antibody every 3 weeks; (c) about 160 mg of the antibody every 3 weeks; (d) about 400 mg of the antibody every 3 weeks; and (e) about 1000 mg of the antibody every 3 weeks. In one embodiment antibody is administered at a dose between 400 and 1000 mg, inclusive. Whether stated or not, any dose range recited herein is intended to be inclusive, i.e. it the doses recited as the boundaries of the ranges are included within the recited dosing range. Preferably, administration of the antibody induces a durable clinical response in the subject. Optionally, administration of the antibody is continued for as long as clinical benefit is observed or until unmanageable toxicity or disease progression occurs. The efficacy of the treatment methods provided herein can be assessed using any suitable means. In one embodiment, the treatment produces at least one therapeutic effect selected from the group consisting of reduction in size of the cancer, reduction in number of metastatic lesions over time, complete response, partial response, and stable disease.

Patients treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a complete response (CR), a partial response (PR), or stable disease (SD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

VIII. Kits and Unit Dosage Forms

Also provided herein are kits that include a pharmaceutical composition containing an anti-fucosyl-GM1 antibody (such as BMS-986012) and/or an anti-huCD137 antibody (BMS-663513), and a pharmaceutically acceptable carrier, in a therapeutically effective amount adapted for use in the preceding methods.

The kits optionally can also include instructions, e.g., comprising administration schedules, to allow a practitioner (e.g., a physician, nurse, or patient) to administer the composition contained therein to administer the composition to a patient having a cancer (e.g., a lung cancer). The kit can also include a syringe.

Optionally, the kits include multiple packages of the single-dose pharmaceutical compositions each containing an effective amount of the antibody for a single administration in accordance with the methods provided above. Instruments or devices necessary for administering the pharmaceutical composition(s) also may be included in the kits. For instance, a kit may provide one or more pre-filled syringes containing an amount of the antibody.

The following examples are merely illustrative and should not be construed as limiting the scope of this disclosure in any way as many variations and equivalents will become apparent to those skilled in the art upon reading the present disclosure.

Example 1

Combination Therapy—Anti-Fucosyl GM1 & Anti-CD137

A combination therapy method of the present invention involving antibodies to fucosyl GM1 and CD137 was tested in the DMS-79 (ATCC CRL-2049) SCLC tumor model in mice. Bepler et al. (1989) *Oncogene* 4:45; Pettengill (1980) *Cancer* 45: 906; Pettengill et al. (1980) *Exp. Cell Biol.* 48:279. Briefly, DMS79 cells were cultured in RPMI with 10% fetal bovine serum (FBS), 2 mM L-glutamine, 15 mg/L sodium bicarbonate, 4.5 g/L glucose, 10 mM HEPES, and 10 µM NaPyr prior to subcutaneous implantation in the right flanks of male C.B17 SCID mice (5 million cells in 0.1 mL phosphate-buffered saline (PBS) and 0.1 mL MATRIGEL® gelatinous protein mixture per flank). When tumors reached a mean or median size of 80-155 $mm^3$ estimated by L×W×H/2 using a digital calipers, mice were randomized into treatment groups (N=8 mice per group).

Anti-fucosyl GM1 antibody BMS-986012 was administered at 3 mg/kg i.p. to mice on days 6, 10, 13, 17 and 20 post-implantation to assess its effectiveness as monotherapy. Because fucosyl GM1 is a ganglioside rather than a protein, and is the same in mice as in humans, there was no need to use a "mouse surrogate" for mouse studies. Anti-muCD137 antibody (a mouse surrogate for BMS-663513) was administered to mice at 1 mg/kg i.p. on days 7, 11, 14, 18 and 21 post implantation to assess its effectiveness as monotherapy.

Combination therapy involved administration of both antibodies according to the same schedule, i.e. anti-CD137 (either 0.1 or 0.3 mg/kg) was administered one day after each dose of anti-fucosyl GM1 (3 mg/kg). A vehicle only control was included. Results are provided at FIG. 1. Anti-CD137 monotherapy was ineffective, while anti-fucosyl GM1 monotherapy significantly reduced tumor growth. Combination therapy, in contrast, virtually eliminated tumor growth at both doses of anti-CD137 tested, demonstrating the synergistic effect of the two antibodies.

Example 2

Combination Therapy—Anti-Fucosyl GM1 & Cisplatin

Figure 2:
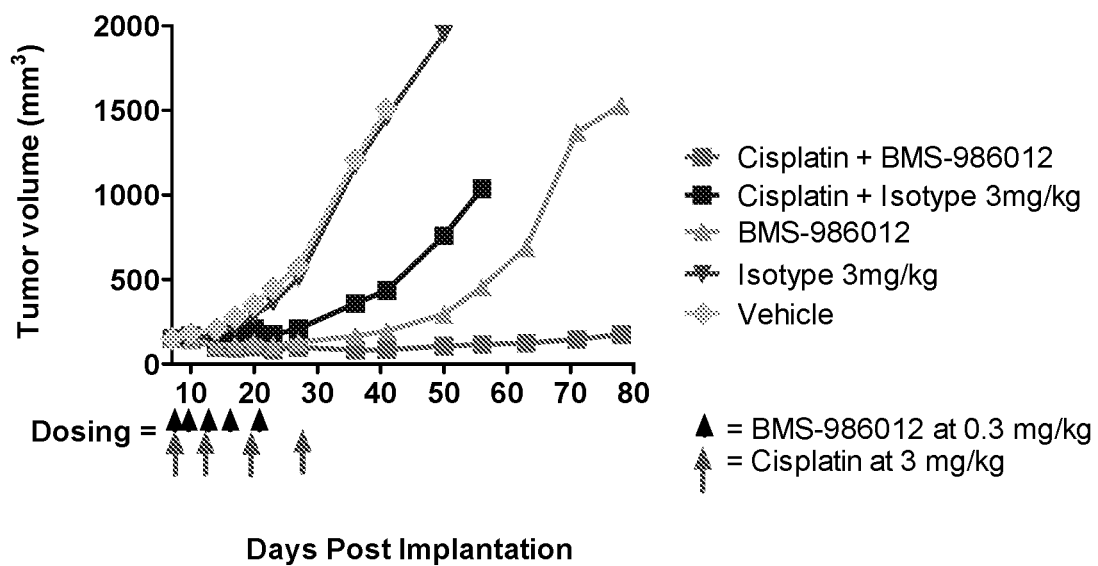
FIG. 2 shows tumor growth in the mouse DMS79 tumor model as a function of treatment with anti-fucosyl GM1 BMS-986012 and/or cisplatin. Median tumor volumes are presented for groups of 8 mice at each data point. See Example 2.

A combination therapy method of the present invention involving antibody to fucosyl GM1 and cisplatin was tested in the DMS-79 SCLC tumor model in mice (N=9 mice per group), essentially as described in Example 1. Anti-fucosyl GM1 antibody BMS-986012 was administered at 0.3 mg/kg i.p. to mice on days 7, 10, 13, 17 and 21 post implantation, and cisplatin was administered at 3 mg/kg on days 7, 14, 21 and 28. Cisplatin was administered in combination with BMS-986012 and with an isotype control antibody at 3 mg/kg as a control. Additional controls included the isotype control antibody alone and a vehicle control. Results are provided at FIG. 2. While both anti-fucosyl GM1 antibody treatment and cisplatin treatment are effective as monotherapy to reduce tumor growth, the combination is significantly more effective—almost stopping tumor growth entirely.

Example 3

Combination Therapy—Anti-Fucosyl GM1 & Etoposide

Figure 3:
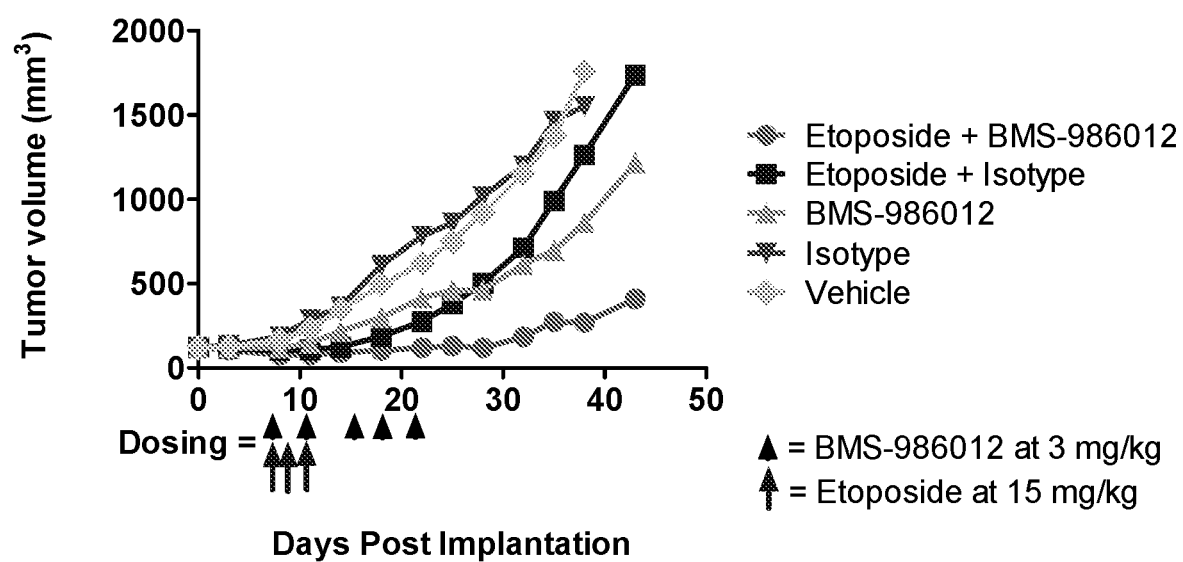
FIG. 3 shows tumor growth in the mouse DMS79 tumor model as a function of treatment with anti-fucosyl GM1 BMS-986012 and/or etoposide. Median tumor volumes are presented for groups of 8 mice at each data point. Combination therapy is significantly more effective than either monotherapy. See Example 3.

A combination therapy method of the present invention involving antibody to fucosyl GM1 and etoposide was tested in the DMS-79 SCLC tumor model in mice (N=9 mice per group), essentially as described in Example 1. Anti-fucosyl GM1 antibody BMS-986012 was administered at 3 mg/kg i.p. to mice on days 7, 11, 15, 18 and 21 post-implantation, and etoposide was administered at 15 mg/kg i.p. on days 7, 9 and 11. Etoposide was administered in combination with BMS-986012 and with an isotype control antibody at 3 mg/kg as a control. Additional controls included the isotype control antibody alone and a vehicle control. Results are provided at FIG. 3. While both anti-fucosyl GM1 antibody treatment and etoposide treatment are somewhat effective as monotherapy to reduce tumor growth, the combination is more effective.

TABLE 1

SUMMARY OF SEQUENCE LISTING

| SEQ ID NO. | Description |
| --- | --- |
| 1 | Anti-FucGM1 Heavy Chain Variable Domain |
| 2 | Anti-FucGM1 Light Chain Variable Domain |
| 3 | Anti-FucGM1 Heavy Chain |
| 4 | Anti-FucGM1 Light Chain |
| 5 | Anti-FucGM1 CDRH1 |
| 6 | Anti-FucGM1 CDRH2 |
| 7 | Anti-FucGM1 CDRH3 |
| 8 | Anti-FucGM1 CDRL1 |
| 9 | Anti-FucGM1 CDRL2 |
| 10 | Anti-FucGM1 CDRL3 |
| 11 | Anti-CD137 Heavy Chain Variable Domain |
| 12 | Anti-CD137 Light Chain Variable Domain |
| 13 | Anti-CD137 Heavy Chain |
| 14 | Anti-CD137 Light Chain |
| 15 | Anti-CD137 CDRH1 |
| 16 | Anti-CD137 CDRH2 |
| 17 | Anti-CD137 CDRH3 |
| 18 | Anti-CD137 CDRL1 |
| 19 | Anti-CD137 CDRL2 |
| 20 | Anti-CD137 CDRL3 |
| 21 | huCD137—NP_001552 |

Antibody sequences in the Sequence Listing include the sequences of the mature variable regions of the heavy and light chains, i.e. the sequences do not include signal peptides.

Equivalents: Those skilled in the art will recognize, or be able to ascertain using no more than routine experimentation, many equivalents of the specific embodiments disclosed herein. Such equivalents are intended to be encompassed by the following claims.

What is claimed is:

1. A method for treating a subject afflicted with cancer, comprising administering to the subject a therapeutically effective combination of:
   a) an anti-fucosyl GM1 antibody, or an antigen-binding portion thereof, comprising;
      i) a heavy chain comprising:
         A) CDRH1 comprising the sequence of SEQ ID NO: 5;
         B) CDRH2 comprising the sequence of SEQ ID NO: 6; and
         C) CDRH3 comprising the sequence of SEQ ID NO: 7; and;
      ii) a light chain comprising:
         A) CDRL1 comprising the sequence of SEQ ID NO: 8;
         B) CDRL2 comprising the sequence of SEQ ID NO: 9; and
         C) CDRL3 comprising the sequence of SEQ ID NO: 10; and
   b) an anti-huCD137 antibody, or an antigen-binding portion thereof, comprising;
      i) a heavy chain comprising:
         A) CDRH1 comprising the sequence of SEQ ID NO: 15;
         B) CDRH2 comprising the sequence of SEQ ID NO: 16; and
         C) CDRH3 comprising the sequence of SEQ ID NO: 17; and;
      ii) a light chain comprising:
         A) CDRL1 comprising the sequence of SEQ ID NO: 18;
         B) CDRL2 comprising the sequence of SEQ ID NO: 19; and
         C) CDRL3 comprising the sequence of SEQ ID NO: 20.

2. The method of claim 1, wherein the anti-fucosyl GM1 antibody is hypofucosylated or non-fucosylated.

3. The method of claim 2, wherein the cancer is lung cancer.

4. The method of claim 3, wherein the lung cancer is small cell lung cancer (SCLC).

5. The method of claim 1, wherein the anti-fucosyl GM1 antibody, or antigen-binding fragment thereof, comprises:

a. a heavy chain variable region comprising the sequence of SEQ ID NO: 1; and
b. a light chain variable region comprising the sequence of SEQ ID NO: 2.

6. The method of claim 5, wherein the anti-fucosyl GM1 antibody is non-fucosylated.

7. The method of claim 6, wherein the anti-fucosyl GM1 antibody is BMS-986012, wherein BMS-986012 comprises heavy and light chains comprising the sequences of SEQ ID NOs: 3 and 4, respectively.

8. The method of claim 5, wherein the anti-fucosyl GM1 antibody is an antibody-drug conjugate.

9. The method of claim 1, wherein the anti-huCD137 antibody, or antigen-binding fragment thereof, comprises:
a. a heavy chain variable region comprising the sequence of SEQ ID NO: 11; and
b. a light chain variable region comprising the sequence of SEQ ID NO: 12.

10. The method of claim 9, wherein the anti-huCD137 antibody is BMS-663513, wherein BMS-663513 comprises heavy and light chains comprising the sequences set forth in SEQ ID NOs: 13 and 14, respectively.

11. The method of claim 10, wherein the anti-fucosyl GM1 antibody is BMS-986012, wherein BMS-986012 comprises heavy and light chains comprising the sequences of SEQ ID NOs: 3 and 4, respectively.

12. The method of claim 1, wherein the anti-fucosyl GM1 antibody, or antigen-binding portion thereof, is administered at a dose between 400 and 1000 mg.

13. The method of claim 12, wherein the anti-huCD137 antibody, or antigen-binding portion thereof, is administered at a dose between 3 and 8 mg.

14. The method of claim 1, wherein the anti-huCD137 antibody, or antigen-binding portion thereof, is administered at a dose between 3 and 8 mg.

15. The method of claim 1, wherein the anti-fucosyl GM1 antibody, or antigen-binding portion thereof, is administered concurrently with administration of the anti-huCD137 antibody, or antigen-binding portion thereof.

16. The method of claim 1, wherein the anti-fucosyl GM1 antibody, or antigen-binding portion thereof, is administered prior to administration of the anti-huCD137 antibody, or antigen-binding portion thereof.

17. The method of claim 16 wherein the anti-fucosyl GM1 antibody, or antigen-binding portion thereof, is administered approximately one day prior to administration of the anti-huCD137 antibody, or antigen-binding portion thereof.

* * * * *

UNITED STATES PATENT AND TRADEMARK OFFICE
CERTIFICATE OF CORRECTION

PATENT NO. : 11,104,739 B2
APPLICATION NO. : 16/093288
DATED : August 31, 2021
INVENTOR(S) : Cardarelli et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this
Thirty-first Day of January, 2023

*Katherine Kelly Vidal*

Katherine Kelly Vidal
*Director of the United States Patent and Trademark Office*